(12) United States Patent
Gilani et al.

(10) Patent No.: US 10,799,333 B2
(45) Date of Patent: Oct. 13, 2020

(54) MAGNETIC ASSISTED IN-SITU TUBULAR STENTGRAFT FENESTRATION

(71) Applicants: Baylor College of Medicine, Houston, TX (US); Texas Heart Institute, Houston, TX (US)

(72) Inventors: Ramyar Gilani, Houston, TX (US); Ourania Preventza, Houston, TX (US); William E. Cohn, Houston, TX (US)

(73) Assignees: Baylor College of Medicine, Houston, TX (US); Texas Heart Institute, Houston, TX (US)

( * ) Notice: Subject to any disclaimer, the term of this patent is extended or adjusted under 35 U.S.C. 154(b) by 434 days.

(21) Appl. No.: 15/531,710

(22) PCT Filed: Dec. 8, 2015

(86) PCT No.: PCT/US2015/064537
§ 371 (c)(1),
(2) Date: May 30, 2017

(87) PCT Pub. No.: WO2016/094430
PCT Pub. Date: Jun. 16, 2016

(65) Prior Publication Data
US 2017/0325934 A1 Nov. 16, 2017

Related U.S. Application Data

(60) Provisional application No. 62/089,592, filed on Dec. 9, 2014.

(51) Int. Cl.
*A61F 2/07* (2013.01)
*A61F 2/95* (2013.01)
*A61F 2/06* (2013.01)

(52) U.S. Cl.
CPC .......... *A61F 2/07* (2013.01); *A61F 2002/061* (2013.01); *A61F 2210/009* (2013.01); *A61F 2220/0025* (2013.01)

(58) Field of Classification Search
CPC ........ A61F 2/95–2/97; A61F 2210/009; A61F 2220/0025; A61F 2/07; A61B 2018/1407; A61B 2018/141; A61B 2002/061
(Continued)

(56) References Cited

U.S. PATENT DOCUMENTS 4,979,939 A * 12/1990 Shiber ...................... A61B 8/12
604/22
6,264,662 B1 * 7/2001 Lauterjung ............... A61F 2/95
606/108

(Continued)

FOREIGN PATENT DOCUMENTS

WO 2002068012 A2 9/2002
WO 2009056644 A1 5/2009

*Primary Examiner* — Kathleen S Holwerda
(74) *Attorney, Agent, or Firm* — Norton Rose Fulbright US LLP

(57) ABSTRACT

A magnet assisted surgical device, system, and method employs magnetic sections, catheters, and guidewires to modify tubular stentgrafts in-situ. One example application provides a more reliable way for surgeons to modify stentgrafts insitu to allow blood flow to continue to branching blood vessels that would otherwise be blocked by the stentgraft itself. One such method includes placing a tip section of the device in the desired location, deploying a stentgraft, placing a magnetic device inside the stentgraft, connecting the magnetic device to the tip section, and excising the portion of the stentgraft held between the magnet and the tip section.

15 Claims, 14 Drawing Sheets

(58) Field of Classification Search
USPC .................................................. 606/108, 185
See application file for complete search history.

(56) References Cited

U.S. PATENT DOCUMENTS

| | | | |
|---|---|---|---|
| 7,066,924 B1 | 6/2006 | Garibaldi et al. | |
| 7,645,273 B2 | 1/2010 | Lualdi | |
| 7,867,270 B2 | 1/2011 | Hartley et al. | |
| 2001/0044622 A1* | 11/2001 | Vardi | A61F 2/954 |
| | | | 606/1 |
| 2004/0002714 A1* | 1/2004 | Weiss | A61F 2/07 |
| | | | 606/108 |
| 2005/0228422 A1* | 10/2005 | Machold | A61B 17/00234 |
| | | | 606/167 |
| 2007/0203572 A1* | 8/2007 | Heuser | A61B 17/11 |
| | | | 623/1.35 |
| 2008/0208309 A1 | 8/2008 | Saeed | |
| 2008/0255475 A1 | 10/2008 | Kondrosky et al. | |
| 2014/0194970 A1* | 7/2014 | Chobotov | A61F 2/954 |
| | | | 623/1.12 |

* cited by examiner

MAGNETIC ASSISTED IN-SITU TUBULAR STENTGRAFT FENESTRATION

CROSS-REFERENCE TO RELATED APPLICATIONS

This application is a national phase application under 35 U.S.C. § 371 that claims priority to International Application No. PCT/US15/64537 filed Dec. 8, 2015, which claims the benefit of priority of U.S. Provisional Patent Application No. 62/089,592 to Gilani et al. filed on Dec. 9, 2014 and entitled "Magnetic Assisted In-Situ Tubular Stentgraft Fenestration," all of which are incorporated by reference.

FIELD OF THE DISCLOSURE

The instant disclosure relates to the use of magnetism to assist in the in-situ fenestration of a tubular stentgraft.

BACKGROUND

An aortic aneurysm refers to the expanding or ballooning of the aorta, the major artery that delivers blood from the heart to the rest of the body. This expansion can result from various genetic conditions, diseases, or some underlying weakness in the wall of the aorta, often as a result of buildup of artheriosclerotic plaque. These aneurysms usually do not initially produce symptoms, however further enlargement can result in pain, numbness, embolism, or rupture often resulting in death. Over ten thousand deaths each year are directly attributable to aortic aneurysms in the United States.

Aneurysms may be treated with the prescription of beta blockers, cessation of smoking, or conventional blood pressure regulation methods, among other treatments. These measures merely slow the growth of the aneurysm, but generally do not totally stop expansion. When the risks associated with surgery are outweighed by the risk of rupture, aortic aneurysms are treated via surgery. Surgical options for the treatment of an aortic aneurysm include traditional open procedures and endovascular therapy. Open surgery involves replacing the affected portion of the aorta with a synthetic graft. Often times, open surgery becomes the only repair option due to various anatomic and patient related factors. However, open surgery of the aorta can have significant physiologic impact which for some patients becomes beyond the threshold of tolerance.

As an alternative to open surgery, endovascular therapy involves the placement of an endovascular stent in the aneurysm. This procedure involves the insertion of the stent into the femoral artery through an incision in the patient's thigh, and from there, into the aorta. The less invasive nature of endovascular therapy results in a reduced physiological impact when compared to open surgery. Generally, the stents used for this procedure are generalized, off-the-shelf products that can be implemented in a standard aortic aneurysm. However, when the aneurysm exists at or near a point in the aorta where a branching artery connects to the aorta, a standard stent is generally not feasible because the stent, in circumventing the aneurysm also circumvents the branch artery as well.

Current solutions for this issue include custom endografts based on precise measurements obtained from CT imaging. These custom endografts generally take weeks to be manufactured and therefore are not a viable option for urgent or emergent cases. Another solution currently available to surgeons is to modify the endograft themselves prior to implantation based on similar precise CT imaging. This process can be difficult and oftentimes imprecise in practice, thus leading to challenges when the modified endograft is introduced. Further, another options available to solve this issue involves the use of chimney, periscope, snorkel, and sandwich graft techniques, commonly referred to as "CHIMPS." This option involves the use of a variety of prefabricated grafts that include additional portions that may be used to route blood to the branch arteries. Although these techniques can achieve repair, they provide less structural stability and can be prone to failure. These problems underscore the need for a fast, reliable method of modifying stents in-situ.

SUMMARY

The present invention is directed to apparatus, methods, and systems for magnetic assisted in-situ fenestration of tubular stentgrafts. Using the apparatuses described herein, a physician who is treating a patient diagnosed with an abdominal aortic aneurysm may insert a magnetic tip section into an artery branching off from the affected artery, inset a stentgraft into the affected artery, insert a magnetic docking section into the stentgraft causing the two magnetic sections to connect, and excise the portion of the stentgraft held between the two magnets thus allowing blood to flow from the affected artery into the branch artery despite the presence of a stentgraft that would otherwise be blocking the branch artery. The in-situ nature may allow for valuable time to be saved without the need for complex, precise CT measurements.

In one embodiment, the fenestration device includes a tip section with two ends and two guidewires. The tip section may be magnetic, with one guidewire running through the tip section from one end to the opposite end, and with the other guidewire attached to the tip section. The tip section may be ogive-shaped, and may comprise neodymium, cobalt, iron, samarium, cobalt, copper, zirconium, alnico, ferrite, or some combination thereof. The guidewires may have a diameter between 0.021 inches and 0.038 inches, or a diameter between 0.014 inches and 0.021 inches. In certain embodiments there may be two catheters, one of which fits around one of the guidewires while the other catheter fits around the other guidewire.

In another embodiment, the fenestration device includes a tip section, a docking section, and a guidewire attached to the tip section. Both the tip section and the docking section have a proximal and a distal end. Further, the tip section has a magnetic distal end, while the docking section has a magnetic proximal end such that the distal end of the tip section and the proximal end of the docking section can be magnetically docked. A catheter may be attached to the distal end of the docking section. Further, the guidewire used may be between 0.014 inches and 0.038 inches. Additionally, a second guidewire may run through both the tip section and the docking section.

Another embodiment of the invention is a system including a tip section with a magnetic distal end, a docking section with a magnetic proximal end, three guidewires, and two catheters. The tip section slidably receives the first guidewire, allowing the first guidewire to run through its central axis. Further, the tip section attaches to the second guidewire, detachably connects to the first catheter, magnetically docks with the proximal end of the docking section which is connected to the second catheter, and slidably receives the third guidewire, allowing the third guidewire to run through its central axis. An electric hot-wire loop may be included that surrounds and is guided by the second catheter, travels along the second catheter up to the docking section, and excises a round section from the material sandwiched between the tip section and the docking section. Further, the tip section may be ogive-shaped; the tip section and the docking section may be made out of neodymium, cobalt, iron, samarium, cobalt, copper, zirconium, alnico, ferrite, or some combination thereof; the guidewires may have a diameter of between 0.021 inches and 0.038 inches or between 0.014 inches and 0.021 inches; or the second guidewire may be attached to the side of the tip section.

Another embodiment of the invention is a method for the in-situ fenestration of tubular stentgrafts through the use of a magnetically assisted fenestration device. The method includes several steps. First, a magnetic tip section is placed into a vessel that branches off of a main vessel. Next, a stentgraft is deployed into the main vessel so the branching vessel is blocked by the stent. A magnetic docking section is then placed inside of the stentgraft. Next, the magnetic tip section is pulled towards the stentgraft enabling it and the magnetic docking station to magnetically dock. The two docked sections are then used as a guide to navigate a fenestration element to the stentgraft where the fenestration element then excises a portion of the stentgraft.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the disclosed system, apparatus, and methods, reference is now made to the following descriptions taken in conjunction with the accompanying drawings.

DETAILED DESCRIPTION

Figure 1:
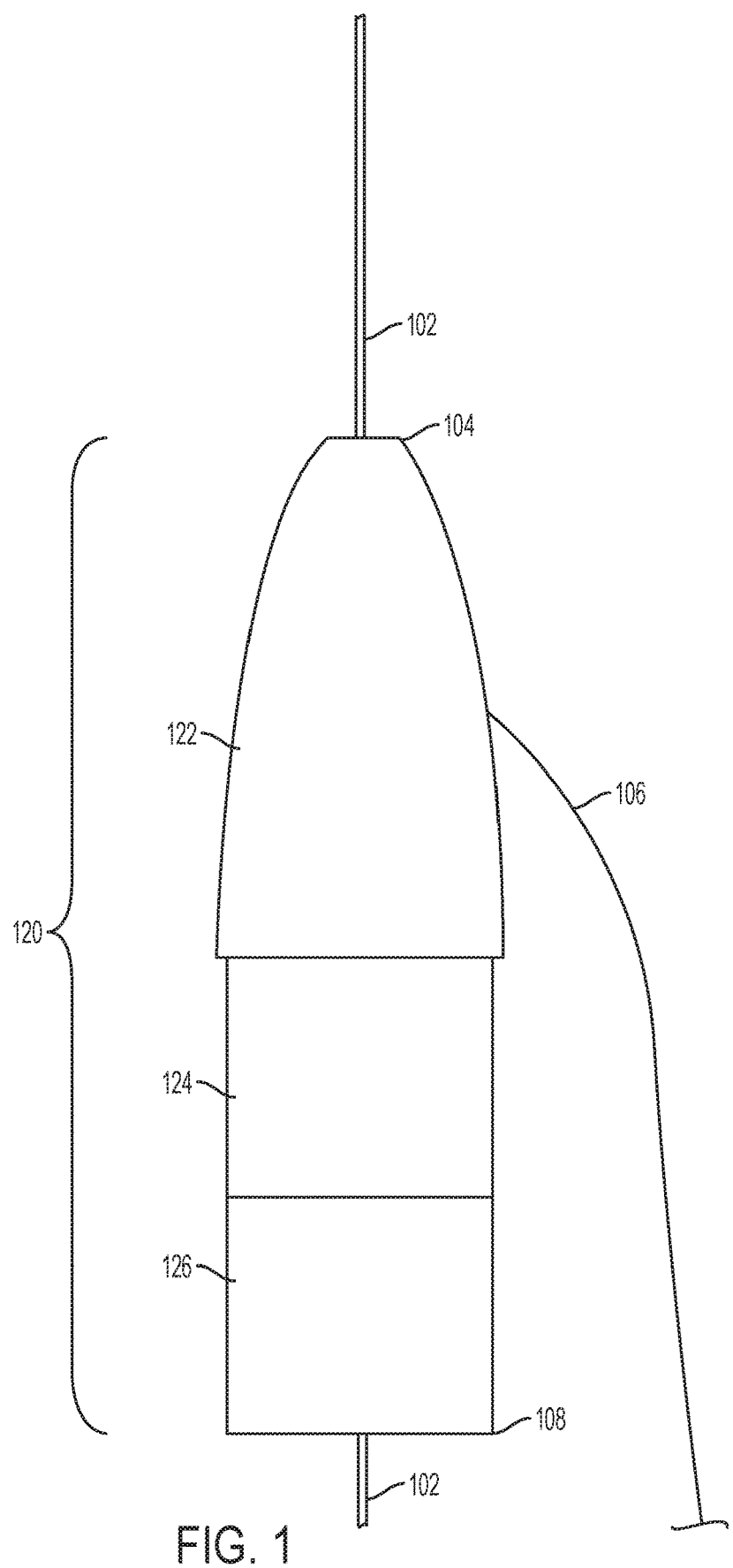
FIG. 1 is an illustration showing a tip section of a fenestration device configured to aid in the in-situ fenestration of tubular stentgrafts according to one embodiment of the disclosure.

FIG. 1 is an illustration showing a tip section of a fenestration device configured to aid in the in-situ fenestration of tubular stentgrafts according to one embodiment of the disclosure. An in-situ fenestration device may include a guidewire 102 that enters the proximal end 104 of the tip section 120 and runs through the body of a tip section 120 of the fenestration device. The guidewire 102 is fed into the vessel where the physician desires to place the tip section 120 and is used to guide the tip section 120 into said vessel. The tip section 120 may comprise a plurality of sub-sections 122, 124, 126. The portion 122 may be made of soft material similar to current catheters to not injury the artery it is being advanced into the artery. The portion 122 may be used to guide a dilator similar to that of a sheath of conventional stents. The portion 124 may serve as the junction between the portions 122 and 126. A second guidewire 106 may be mounted to the tip section 120, and may be affixed to any part of the tip section 120. The second guidewire 106 may be used, once the tip section 120 is in place, to pull the tip section 120 back out its initial placing. One embodiment is shown in FIG. 1 wherein the guidewire 106 is attached to the side of the tip section 120. The guidewire 102 may exit the tip section 120 at the distal end 108.

Figure 2:
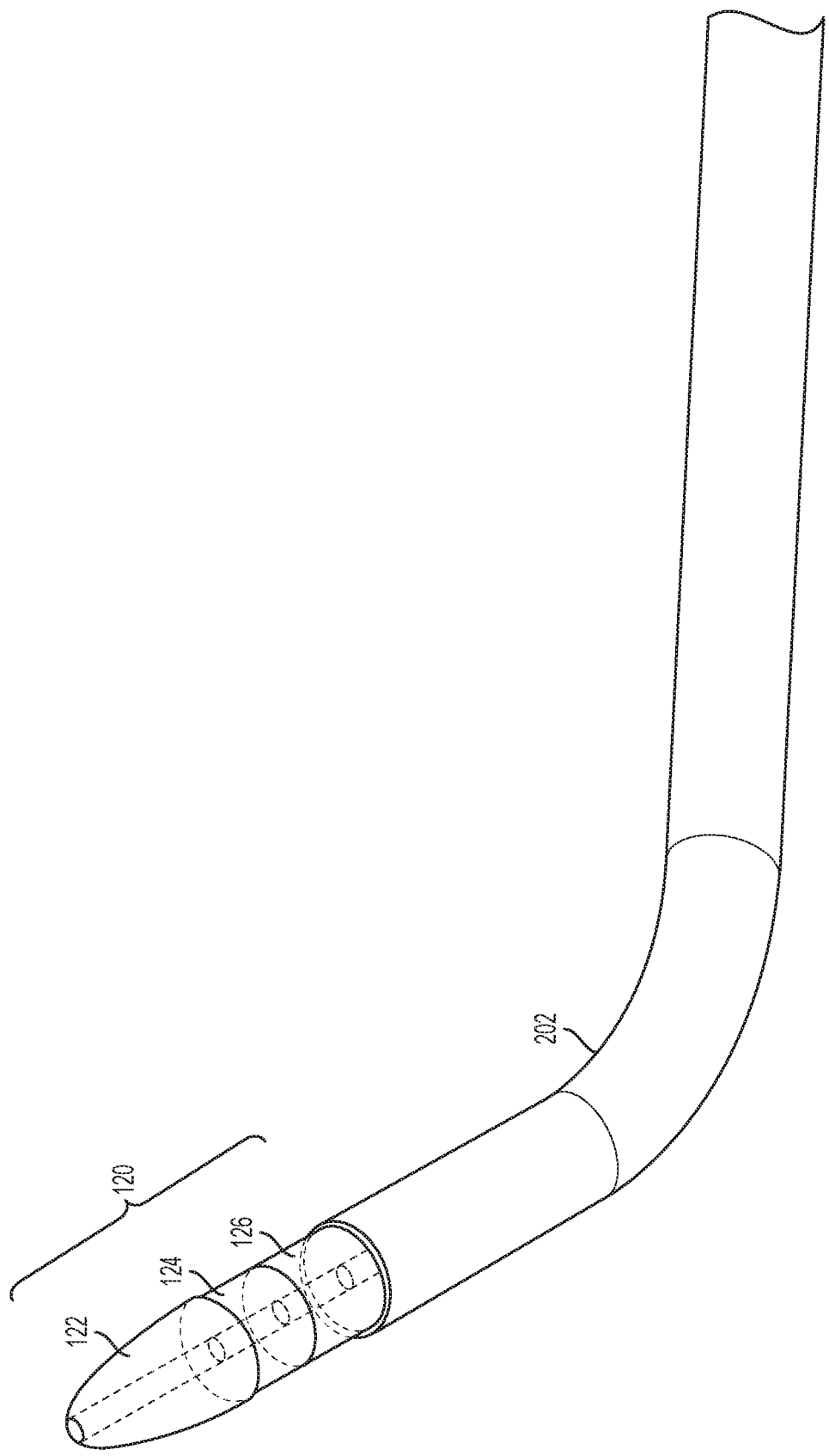
FIG. 2 is an illustration showing a tip section of a fenestration device connected to a catheter according to one embodiment of the disclosure.

The in-situ fenestration device may include additional elements such as catheters to aid in the insertion of guidewires into a patient. FIG. 2 is an illustration showing a tip section of one such fenestration device configured to aid in the in-situ fenestration of tubular stentgrafts according to one embodiment of the disclosure. In this embodiment, the fenestration device may include a catheter 202 which is detachably connected to the tip section 120. The catheter 202 is used by the physician to help guide the tip section 120 along the guidewire 102 so that the tip section can be initially placed in the desired location.

Figure 3:
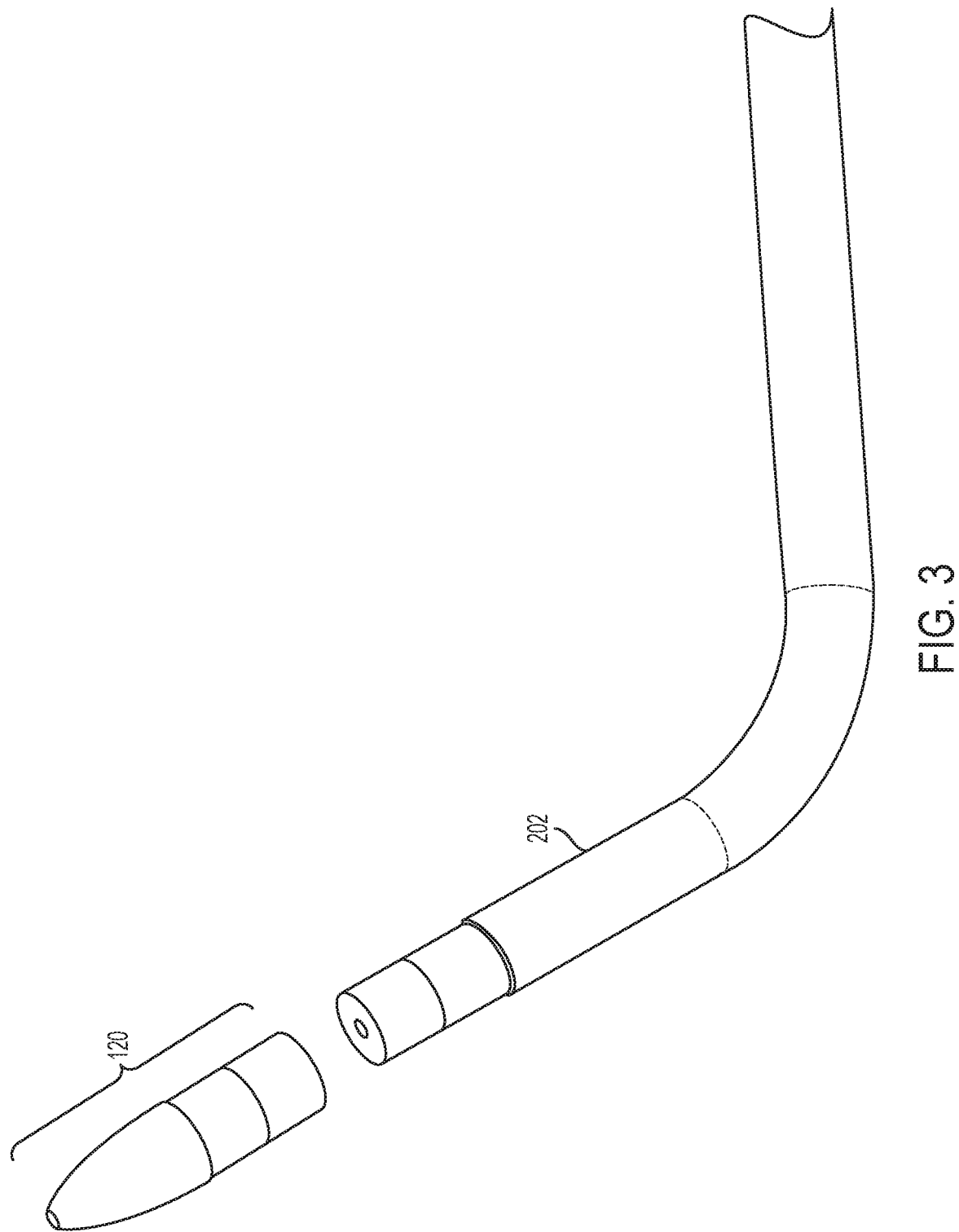
FIG. 3 is an illustration showing a tip section of a fenestration device detached from a catheter according to one embodiment of the disclosure.

The tip section 120, in order to be positioned in the desired location, may be detachable from the catheter(s) themselves. For example, FIG. 3 is an illustration showing a tip section of a fenestration device configured to aid in the in-situ fenestration of tubular stentgrafts according to one embodiment of the disclosure wherein, the tip section 120 is shown detached from the catheter portion 202 of the device. The detachment of the catheter allows for the tip section 120, once in the desired location to be left there, while the catheter 202 is then removed from the patient.

Figure 4:
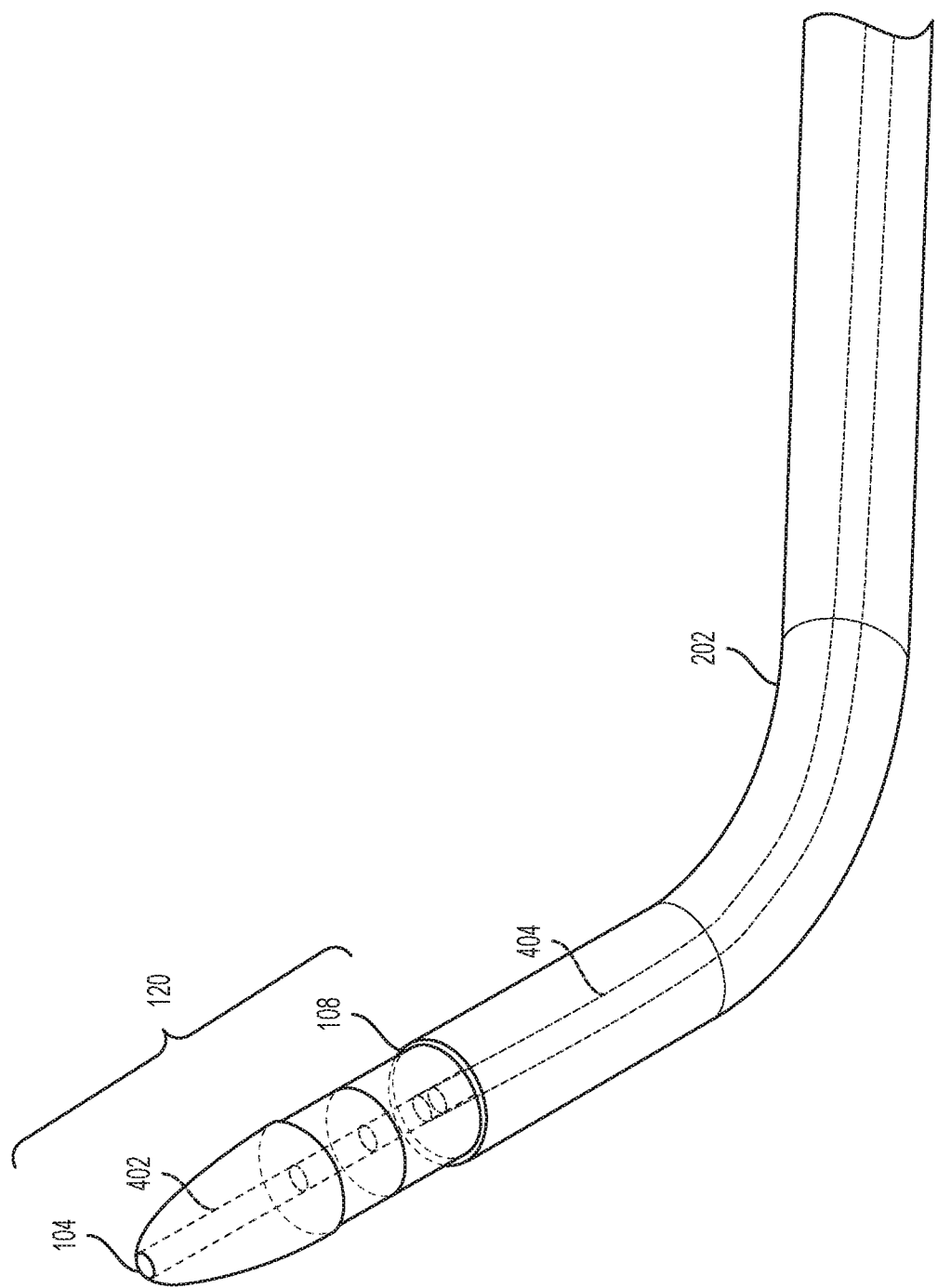
FIG. 4 is an illustration showing a tip section of a fenestration device according to one embodiment of the disclosure wherein an inner catheter, an outer catheter, and an inner channel within the tip section are visible.

Further, the tip section 120 and any accompanying catheters may allow for guidewires to pass coaxially through them. For example, FIG. 4 is an illustration showing a tip section of a fenestration device configured to aid in the in-situ fenestration of tubular stentgrafts according to one embodiment of the disclosure in which the tip section 120 may have having a proximal end 104 and a distal end 108. A tubular lumen 402 may extend through the tip section 120 from the proximal end 104 to the distal end 108. The tubular lumen 402 would allow for guidewires to be passed coaxially through the tip section 120 and any attached catheters. Two coaxial catheters 404, 202 may be detachably connected to the distal end 108 of the tip section 120 of the fenestration device. The smaller catheter 404 may be either independent from or attached to the larger catheter 202. These catheters 404, 202 allow for a guidewire 102 to be passed through up the catheters 404, 202 and the tip section 120 in order to aid the physician in placing the tip section 120 into the desired location before detaching the catheters and removing them from the patient. The catheters 404 (and catheter 706 described below) ay be sized such that their lumen is completely occluded by the guide wire, such as sizes of 0.035 or 0.038.

Figure 5:
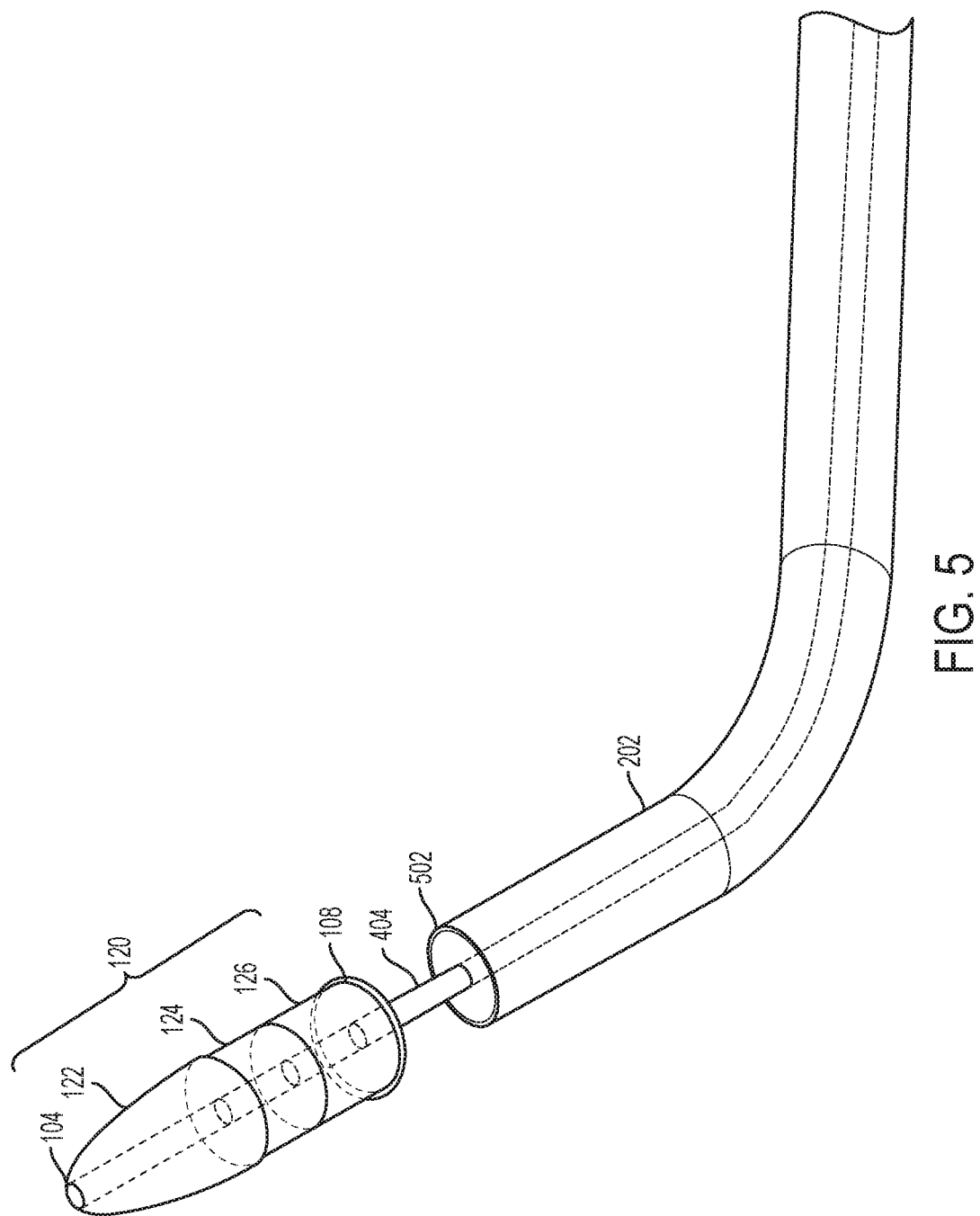
FIG. 5 is an illustration showing a tip section of a fenestration device according to one embodiment of the disclosure wherein an outer catheter has been detached while an inner catheter remains connected to the tip section.

The present invention may include features that provided flexibility and options to physicians when practicing the disclosed fenestration device. For example, FIG. 5 is an illustration showing a tip section 120 configured so that it may be detached from a catheter 202. The proximal end of the detached catheter 502, and the catheter itself 202, may still surround the coaxial inner catheter 404. In this depiction of an embodiment, the inner catheter 404 may still be detachably connected to the distal end 108 of the tip section 120 of the fenestration device. The independent detachability may allow physicians more options to handle their patient's individual needs or more effectively respond to situations that arise during the procedure.

Figure 6:
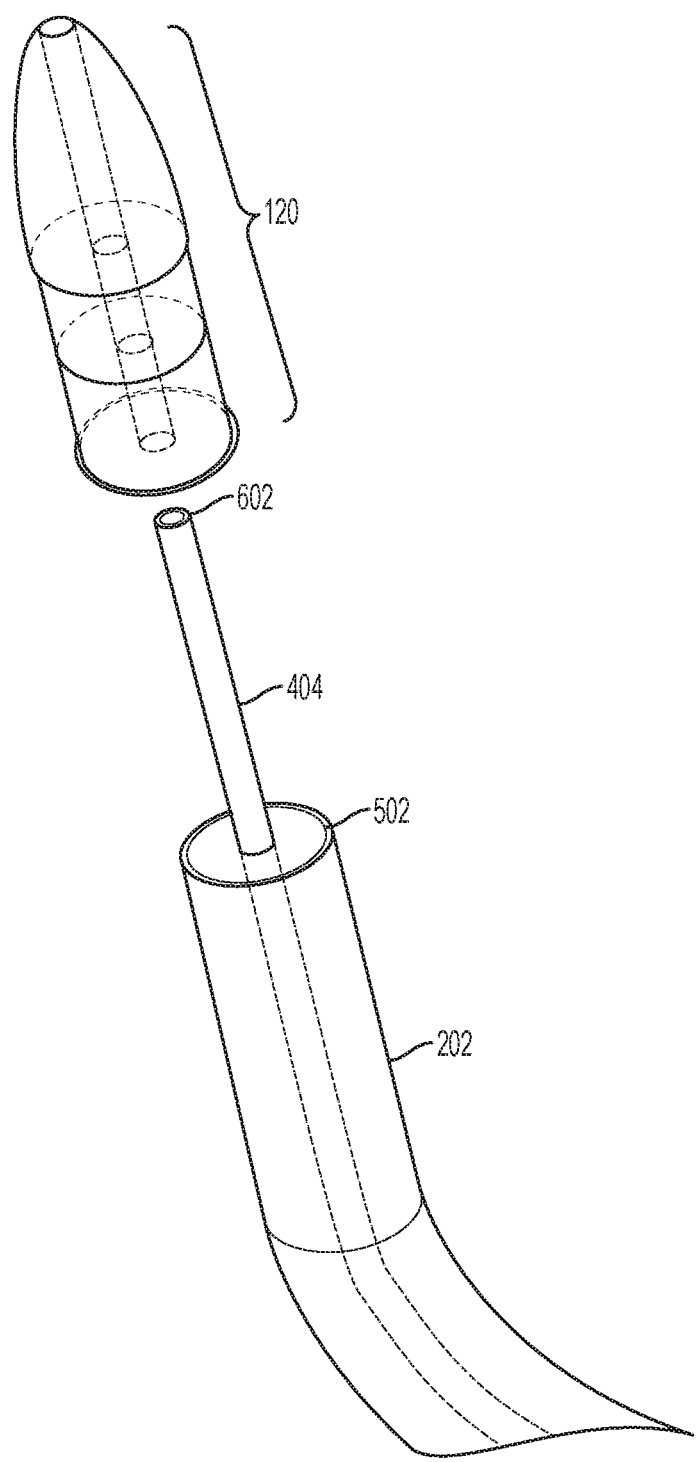
FIG. 6 is an illustration showing a tip section of a fenestration device according to one embodiment of the disclosure wherein both an outer catheter and an inner catheter have been detached from the tip section.

Each element of the apparatus may be independent from each other element, while simultaneously allowing for them to interact, connect to, or be guided by other elements. For example, FIG. 6 is an illustration showing a tip section 120 according to one embodiment of the disclosure that has been detached from both the proximal end of the inner catheter 602 and the proximal end of the outer catheter 502. Therefore, the inner catheter 404 and the outer catheter 202 may both be independent and detachable from the tip section 120 of the fenestration device.

In reference to the guidewires, in one embodiment of the disclosure, the first guidewire 102 may have a diameter of 0.035 inches (0.89 mm), but in other embodiments the first guidewire 102 may have a diameter of 0.014 inches (0.36 mm), 0.018 inches (0.46 mm), 0.021 inches (0.53 mm), 0.025 inches (0.64 mm), 0.032 inches (0.81 mm), or 0.038 inches (0.97 mm). Further, in one embodiment of the disclosure, the second guidewire 106 may have a diameter of 0.014 inches (0.36 mm), but in other embodiments the second guidewire 106 may have a diameter of 0.018 inches (0.46 mm), 0.021 inches (0.53 mm), 0.025 inches (0.64 mm), 0.032 inches (0.81 mm), 0.035 inches (0.89 mm), or 0.038 inches (0.97 mm). Because all guidewire sizes are viable, all suitable guidewires are contemplated and the choice of which to use depends on the specific patient being treated and the specifics of that patient's condition.

With regards to the tip section 120, the first guidewire 102 runs coaxially through the tubular lumen 402 of the tip section 120. In this embodiment, the first guidewire 102 is not connected to the tip section 120, thus allowing the tip section to slide freely along the guidewire 102. Also according to this embodiment, the second guidewire 106 is permanently affixed to the side of the tip section 120. The second guidewire 106 may be attached at such an angle to easily allow for the second guidewire to extend distally along the same path as the first guidewire 102, large catheter 202, and small catheter 404. In one embodiment, the second guidewire 106 is attached to the tip section via vibration welding. However, all suitable methods of attachment are contemplated. For example, in one embodiment of the disclosure, the second guidewire 106 is attached by inserting the guidewire 106 into a channel on the tip section and kinking the guidewire 106 such that the guidewire 106 cannot be removed from the tip section 120 when force is applied to either. In yet another embodiment, the guidewire 106 may be glued to the tip section 120.

The distal end 108 may be magnetic. The tip section 120 might not be a homogeneous material, but instead may have the distal end 108 alone made of a magnetic material. Alternatively, the tip section 120 as a whole may be magnetic and thus may be made of a single material. In one embodiment, the magnetic portion of the tip section 120 is comprised of one or more rare earth metals. One skilled in the art would understand rare earth metals to identify a type of strong permanent magnets made from combinations or alloys of rare earth elements. Such rare earth elements include, but are not limited to Scandium (Sc), Yttrium (Y), Lanthanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), and Lutetium (Lu). Additionally, one skilled in the art would understand that in addition to these rare earth elements, rare earth magnets may comprise additional elements including, but not limited to, Iron (Fe), Nickel (Ni), Cobalt (Co), Aluminum (Al), Copper (Cu), Titanium (Ti), and Boron (B). These magnetic characteristics may allow the tip section 120 to further interact and magnetically dock with other portions.

The tip section may be ogive-shaped. A person having ordinary skill in the art would understand the description "ogive" to refer to an object having a roundly tapered end. For example, the tip section 120 of the device is in the shape of a bullet. This shape allows the bullet to more easily pass within vessels by reducing the risk of the vessels being damaged. Additionally, the tip section 120 may include a tubular lumen 402 running coaxially from its proximal end 104 to its distal end 108. The tubular lumen 402 may have a diameter of 0.035 inches, but may alternatively have a diameter of 0.014 inches (0.36 mm), 0.018 inches (0.46 mm), 0.021 inches (0.53 mm), 0.025 inches (0.64 mm), 0.032 inches (0.81 mm), or 0.038 inches (0.97 mm) to fit the various guidewire sizes that may be used in conjunction with the tip section 120.

In reference to the catheters, the small catheter 404 may run coaxially with the larger catheter 202. Both the small catheter 404 and the larger catheter 202 may be detachably connected from the tip section 120. The size of the larger catheter 202 (and larger catheter 708 shown below) may be dependent upon the diameter of the magnets that are selected and based on a diameter of the vessel being cannulated. In one embodiment, the small catheter 404 is French gauge 4 catheter, but in other embodiments the small catheter 404 may be French gauge 3, 5, 6, or 7. Because all catheter sizes are viable, all suitable catheters are contemplated and the choice of which to use depends on the size guidewires being used, the specific patient being treated, and the specifics of that patient's condition.

In addition to the tip section 120, the apparatus may include a complementary docking section that magnetically interacts with the tip section. These two sections, when acting together, may be used to isolate a portion of the stentgraft such that the portion may be excised.

Figure 7:
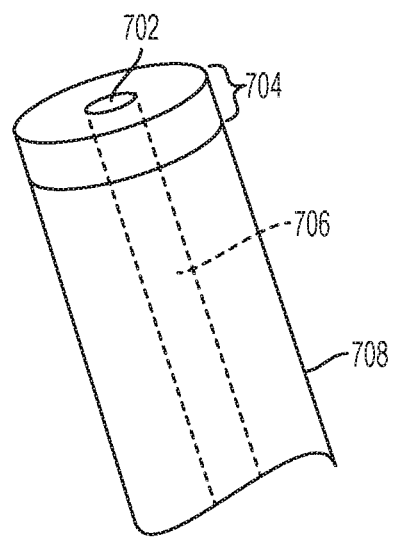
FIG. 7 is an illustration showing a docking section of a fenestration device according to one embodiment of the disclosure wherein the docking station is connected to an inner catheter and an outer catheter.

FIG. 7 is an illustration showing a docking section of a fenestration device configured to aid in the in-situ fenestration of tubular stentgrafts according to one embodiment of the disclosure. A docking section 704 is connected to two coaxial catheters: a large catheter 708 and a smaller catheter 706. The lumen of the smaller catheter continues through the tubular lumen 702 that runs through the docking section 704 such that a guidewire may coaxially run thought both the docking section 704 and the catheters 706, 708. The large catheter 708 connects to the docking station and surrounds the smaller catheter 706.

As with the tip section 120, the docking section 704 may be magnetic. In one embodiment, the docking section 704 is comprised of one or a combination of rare earth metals. One skilled in the art would understand rare earth metals to identify a type of strong permanent magnets made from combinations or alloys of rare earth elements. Such rare earth elements include, but are not limited to Scandium (Sc), Yttrium (Y), Lanthanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), and Lutetium (Lu). Additionally, one skilled in the art would understand that in addition to these rare earth elements, rare earth magnets may comprise additional elements including, but not limited to, Iron (Fe), Nickel (Ni), Cobalt (Co), Aluminum (Al), Copper (Cu), Titanium (Ti), and Boron (B). These magnetic characteristics allow the docking section to further magnetically interact with a tip section 120.

The docking section 704 may have a cylindrical shape and connect with catheters 706, 708 on one of the two flat cylinder faces. The docking section 704 may additionally have a tubular lumen 702 that runs from one cylinder face to the opposite face in order to allow guidewires to be passed through it. In one embodiment, the tubular lumen 702 has a diameter of 0.035 inches, but may alternatively have a diameter of 0.014 inches (0.36 mm), 0.018 inches (0.46 mm), 0.021 inches (0.53 mm), 0.025 inches (0.64 mm), 0.032 inches (0.81 mm), or 0.038 inches (0.97 mm) to fit the various guidewire sizes that may be used in conjunction with the docking section 704.

In reference to the catheters that could be used in connection with a docking section 704, in one embodiment, the small catheter 706 runs coaxially with the larger catheter 708. Both the small catheter 706 and the larger catheter 708 may be permanently attached to the docking section 704. In one embodiment, the small catheter 706 is French gauge 4 catheter, but in other embodiments the small catheter 706 may be French gauge 3, 5, 6, 7, or 8. Because all catheter sizes are viable, all suitable catheters are contemplated and the choice of which to use depends on the size guidewires being used, the specific patient being treated, and the specifics of that patient's condition.

Figure 8:
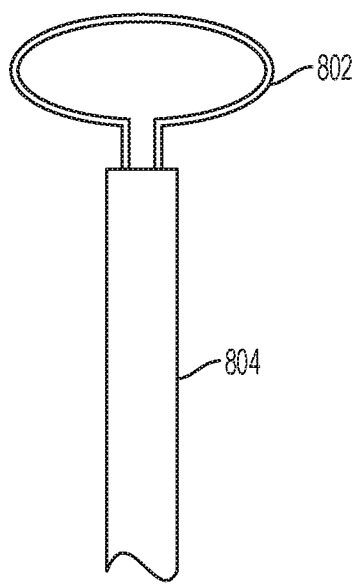
FIG. 8 is an illustration showing an electric hot-wire loop of a fenestration device according to one embodiment of the disclosure.

The apparatus may additionally include an element that has the capability of excising a portion of the surgical stentgrafts used by the physician to treat an aneurysm. FIG. 8 in an illustration showing an electric hot-wire loop section of a fenestration device configured to aid in the in-situ fenestration of tubular stentgrafts according to one embodiment of the disclosure. The fenestration portion of the electric hot-wire loop 802 may be located at the proximal end of the body of the fenestration section 804. The electric hot-wire loop section of the fenestration device creates heat for the purpose of cutting material by applying an electrical current across an exposed wire loop 802 thereby causing the wire loop 802 to generate heat. The current necessary to cause the fenestration portion of the electric hot-wire loop 802 to be used as a cutting implement is fed to the loop 802 through wires running up the body of the fenestration section 804. The loop form of the fenestration portion 802 allows for a guidewire or catheter to run through the loop and thus guide the loop to a desired location.

Figure 9:
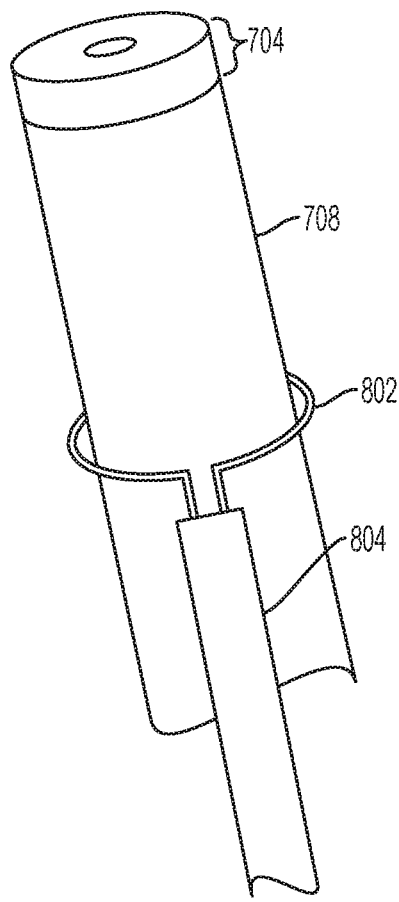
FIG. 9 is an illustration showing the interaction between an electric hot-wire loop section and a docking section of a fenestration device according to one embodiment of the disclosure.

The electric hot-wire loop and the docking section may be configured to interact with one another. FIG. 9 is an illustration showing an embodiment of such an interaction configured to aid in the in-situ fenestration of tubular stentgrafts. A fenestration portion of an electric hot-wire loop 802 surrounds and is guided by a catheter 708 attached to a docking section 704 of the device. The body of the fenestration section 804 extends distally, approximately parallel to the catheter 708. In one embodiment, the fenestration portion of the electric hot-wire loop 802 may be larger in diameter than the outer diameter of the catheter 708 so that the hot-wire loop 802 fits around and can be slid along the catheter 708.

Figure 10:
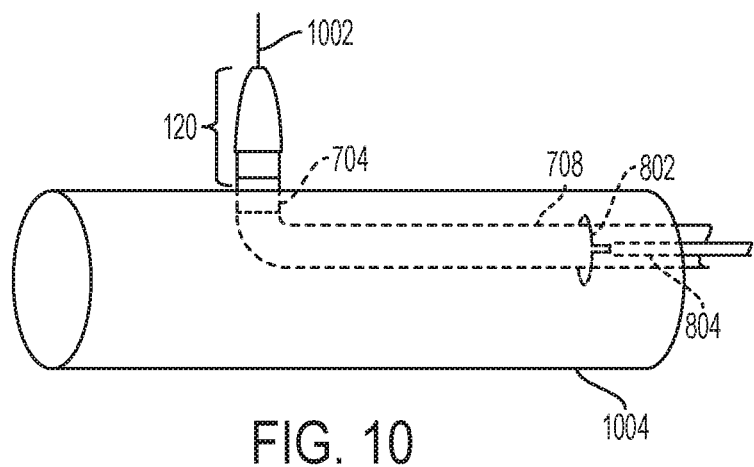
FIG. 10 is an illustration showing the interaction between a tip section of a fenestration device, a docking section of a fenestration device, an electric hot-wire loop section of a fenestration device, and a stentgraft, according to one embodiment of the disclosure.

Bringing many of the described components together, FIG. 10 is an illustration showing an embodiment of the interaction between a tip section 120, a docking section 704, and a hot-wire loop section of a fenestration device 802 configured to aid in the in-situ fenestration of tubular stentgrafts according to one embodiment of the disclosure. A tip section 120 is positioned on the exterior of a tubular stentgraft 1004. The tip section 120 is magnetically docked with a docking section 704 which is positioned on the interior of the tubular stentgraft 1004 directly opposite the tip section 120. A catheter 708 is attached to the docking section 704 and said catheter 708 extends out the distal end of the tubular stentgraft 1004. The fenestration portion of an electric hot-wire loop 802 surrounds and is guided by the catheter 708. The body of the fenestration portion 804 may extend distally from the fenestration portion of the electric hot-wire loop 802, and runs approximately parallel to the catheter 708. The fenestration portion of the electric hot-wire loop 802 may be fed up along the catheter 708 until it comes into contact with the portion of the stentgraft nearby the docking section 704. Once the fenestration portion 802 comes into contact with the stentgraft, the hot-wire loop 802 may be activated, thereby excising the portion of the stentgraft held between the tip section 120 and the docking section 704. A sharp-tipped guidewire 1002 runs through the tip section 120, the tubular stentgraft 1004, the docking section 704, and the catheter 708. The sharp-tipped guidewire 1002 is used to ensure that the tip section 120, and the docking section 704 are lined up in a desired configuration such that the lumen within each piece allows for the sharp-tipped guidewire 1002 to run through both sections.

Figure 11:
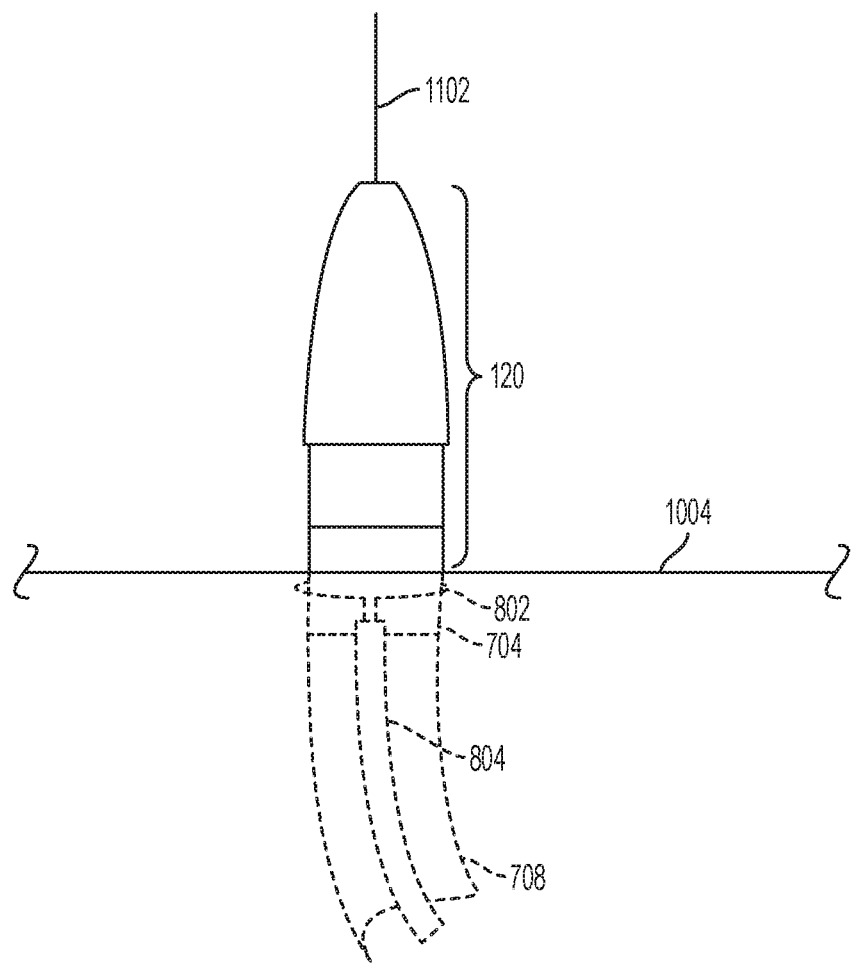
FIG. 11 is an illustration showing the configuration of a fenestration device at the time where a portion of a stentgraft is excised, according to one embodiment of the disclosure.

Further illustrating the interaction between certain components, FIG. 11 shows an embodiment of how a hot-wire loop section of a fenestration device excises a portion of a tubular stentgraft. A tip section 120 is situated directly opposite from a magnetically docked docking section 704, with only a tubular stentgraft 1004 separating the two sections. A fenestration portion of an electric hot-wire loop 802 has advanced along the catheter 708 it surrounds such that the fenestration portion makes contact with the tubular stentgraft 1004, thus excising a portion of the stentgraft. The body of the fenestration section 804 runs distally away from the fenestration portion 802 approximately parallel to the catheter 708. A sharp-tipped guidewire 1002 runs coaxially through the tip section 120, the tubular stentgraft 1004, the docking section 704, and the catheter 708.

Figure 12:
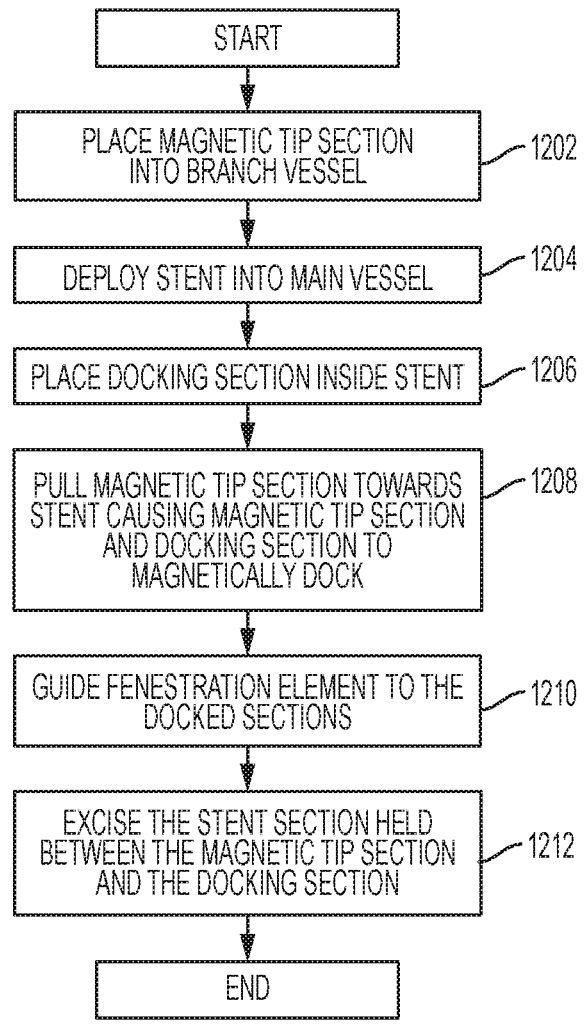
FIG. 12 is a block diagram explaining the steps involved in magnet assisted in-situ fenestration of a stentgraft according to one embodiment of the disclosure.

A method of magnet assisted in-situ fenestration of a stentgraft may be described with respect to the flow chart of FIG. 12. A tip section 120 is placed into a branch vessel at block 1202. A surgical stentgraft 1004 is deployed into the main vessel at block 1204 thereby blocking the branch vessel containing the tip section 120. Next, the docking station 704 is placed into the stentgraft 1004 at block 1206. The tip section 120 is then pulled towards the stentgraft 1004 such that it causes the tip section 120 and the docking section 704 to magnetically dock at block 1208. Next, an electric hot-wire loop 802 is guided at block 1210 to the location where the tip section 120 and the docking section 704 are docked. Then, the electric hot-wire loop is used to excise the stentgraft portion held between the tip section 120 and the docking section 704 at block 1212.

Figure 13:
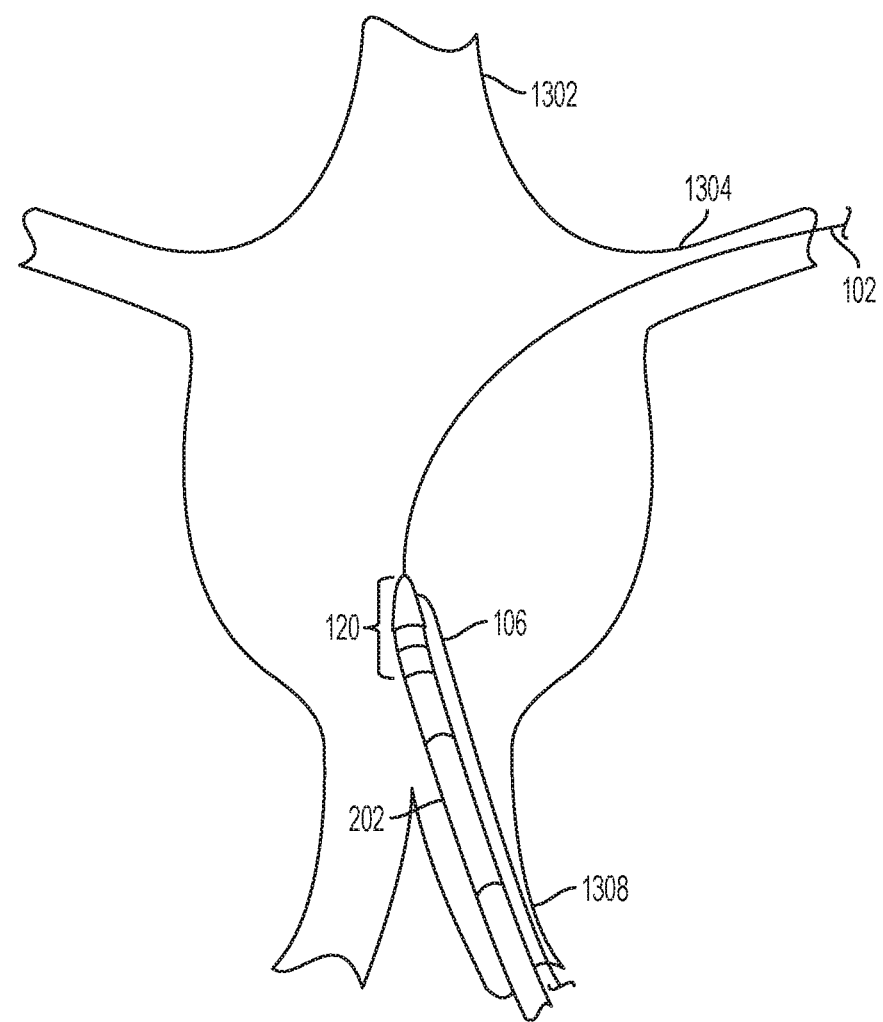
FIG. 13 is an illustration showing a tip section of a fenestration device being positioned in the desired location in vivo, according to one embodiment of the disclosure.
Figure 14:
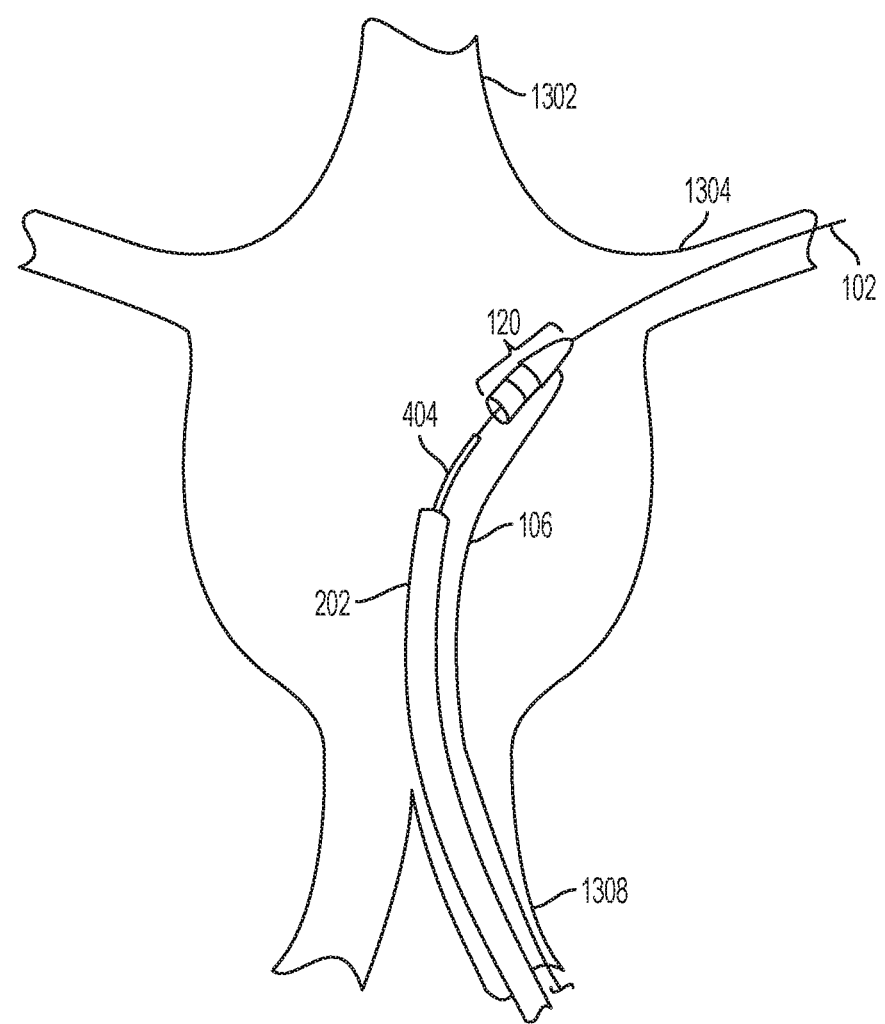
FIG. 14 is another illustration showing a tip section of a fenestration device being positioned in the desired location in vivo, according to one embodiment of the disclosure.
Figure 15:
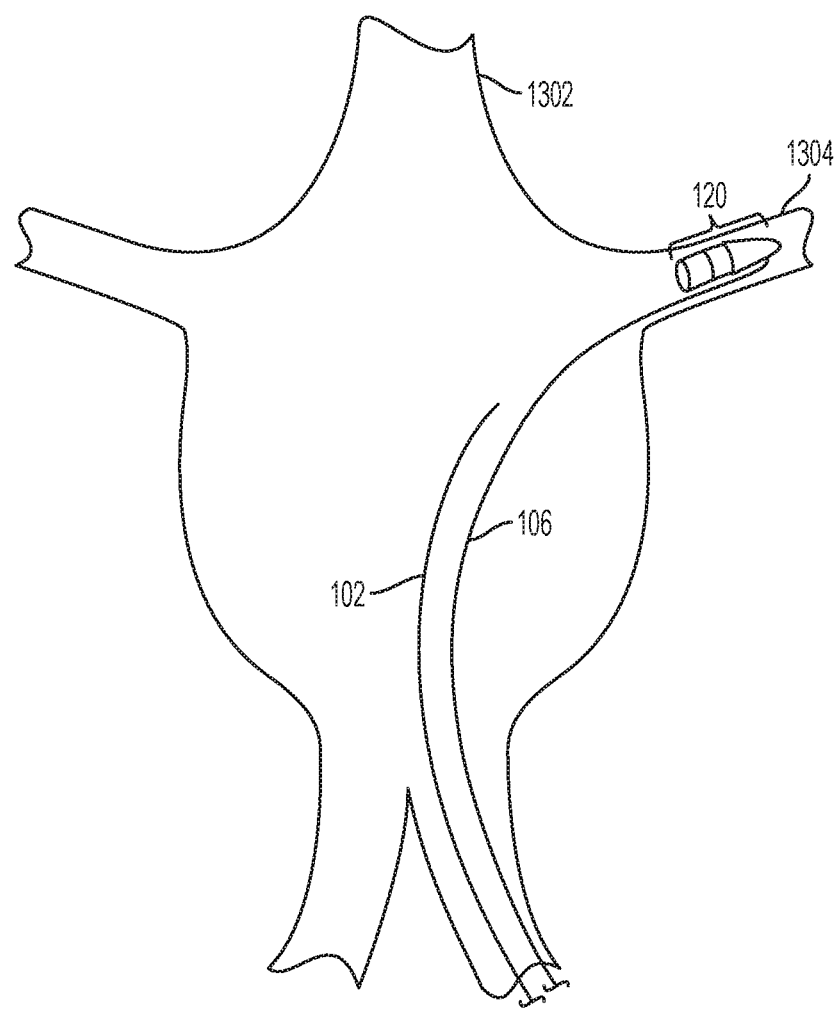
FIG. 15 is yet another illustration showing a tip section of a fenestration device being positioned in the desired location in vivo, according to one embodiment of the disclosure.

Further explaining initial steps of the method in certain embodiments, FIG. 13 illustrates how and where the tip section 120 is placed into the desired location according to one embodiment of the disclosure. Initially, a guidewire 102 may be passed up an entry vessel 1308, through the main vessel 1302, and into a branching vessel 1304. Then, a tip section 120 along with any detachably connected catheters 202 may be passed along the guidewire 102. A guidewire 106 may be attached to the side of the tip section 120. FIG. 14 continues the illustration of FIG. 13 according to one embodiment of the disclosure. In FIG. 14, the tip section 120 may be detached from both a small catheter 404 and a larger catheter 202. Next, the two catheters 202, 404 may then be removed from the patient's body. FIG. 15 continues the illustration of FIG. 13 and FIG. 14, and demonstrates the side-attached guidewire 106 being used to advance the tip section 120 along the guidewire 102 until the tip section 120 is placed as deeply into the branching vessel 1304 as the vessel diameter will permit. A catheter may then be placed over the side-attached guidewire 106 in order to increase column strength to further enable the advancement of the tip section 120 along the guidewire 102. Once the tip section 120 is in the desired location, the guidewire 102 may be withdrawn from the branching vessel and removed from the patient's body.

Figure 16:
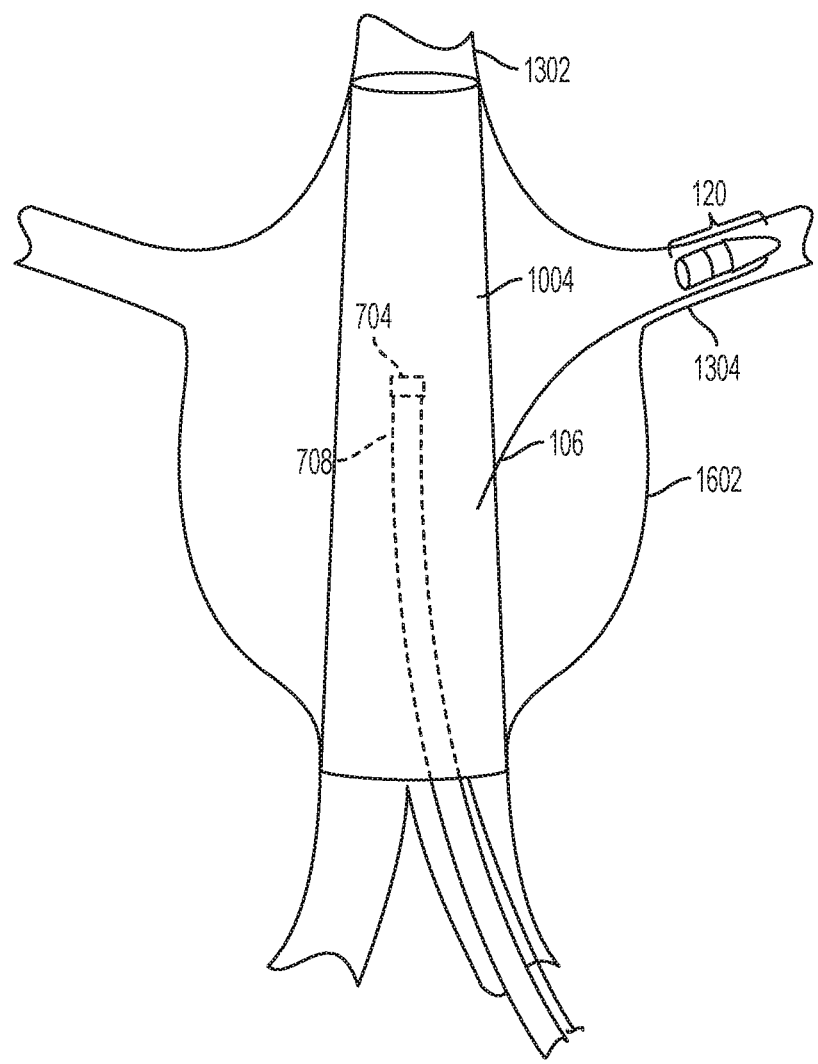
FIG. 16 is an illustration showing the placement of a stentgraft and the use of a docking section of a fenestration device, according to one embodiment of the disclosure.
Figure 17:
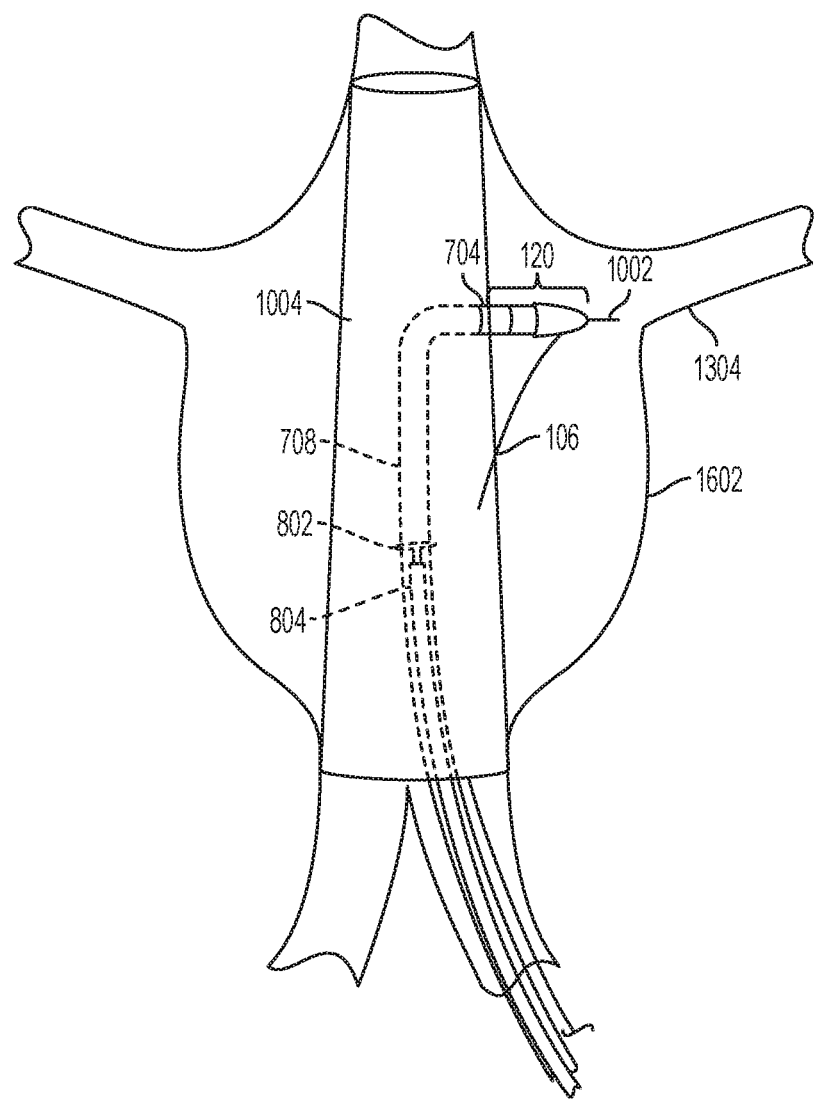
FIG. 17 is an illustration showing the final configuration of a fenestration device before a portion of the stentgraft is excised, according to one embodiment of the disclosure.

FIG. 16 further illustrates how to excise the desired portion of the stentgraft 1004 once the tip section is in place, according to one embodiment of the disclosure. Once the tip section 120 is in place in the branching vessel 1304, a stentgraft 1004 may be deployed in a position to bypass the aneurysm 1602 that has occurred in the main vessel 1302. Once the stentgraft 1004 is in place, a docking section 704 along with at least one attached catheter 708 may be passed into the stentgraft. FIG. 17 continues the illustration of FIG. 16. In FIG. 17, one embodiment of the disclosure is shown as the side-mounted guidewire 106 is pulled causing the tip section 120 to be pulled towards the stentgraft 1004. As the tip section 120 comes into contact with the stentgraft 1004, it may magnetically dock with the docking section 704 with only a portion of the stentgraft 1004 held between the tip section 120 and the docking section 704. Once the magnetic docking as occurred, a sharp-tipped guidewire 1002 may be passed through any catheter 708 attached to the docking section 704, the docking section 704, the portion of the stentgraft held between the two magnets, and the tip section 120. The sharp-tipped guidewire 1002 in this context is used to ensure that the tip section 120 and the docking section 704 are lined up in the desired configuration. Lastly, an electric hot-wire loop 802, 804 may be passed over the catheter 708 until it comes into the contact with the stentgraft 1004, where it excises the portion held between the tip section 120 and the docking section 704.

According to one embodiment of the disclosure, the main vessel 1302 is the patient's aorta. The branching vessel 1304 may be a renal artery, but in other embodiments the branching vessel 1304 may include the gonadal arteries, lumbar arteries, inferior or superior mesenteric arteries, median sacral artery, or the celiac trunk. In one embodiment, the entry vessel 1308 refers to one of the common iliac arteries.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present invention, disclosure, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An apparatus, comprising:
   a tip section having a proximal end and a distal end, wherein at least a portion of the tip section is magnetic;
   a first guidewire extending coaxially through the tip section from the distal end to the proximal end;
   a second guidewire attached to the tip section;
   a first catheter, wherein the first catheter surrounds the first guidewire;
   a second catheter; and an electric hot-wire loop surrounding the second catheter and extending along the second catheter up to a docking section, wherein the electric hot-wire loop is configured to excise a substantially round section from material held between the tip section and the docking section.

2. The apparatus of claim 1, wherein the tip section is ogive-shaped.

3. The apparatus of claim 1, wherein the tip section comprises at least one rare earth magnet.

4. The apparatus of claim 1, wherein the tip section comprises material selected from a group consisting of neodymium, cobalt, iron, samarium, copper, zirconium, aluminum, nickel, and some combination thereof.

5. The apparatus of claim 1, wherein the first guidewire has a diameter of between 0.021 inches and 0.038 inches.

6. The apparatus of claim 1, wherein the second guidewire has a diameter of between 0.014 inches and 0.021 inches.

7. The apparatus of claim 1, wherein the second guidewire is attached to a side of the tip section.

8. The apparatus of claim 1, wherein the distal end of the tip section and a proximal end of the docking section are magnetic such that the tip section and the docking section are configured to be magnetically docked.

9. A system for in-situ fenestration of tubular grafts, comprising:
   a tip section having a proximal end and a distal end, wherein the distal end is magnetic;
   a docking section having a proximal end and a distal end, wherein the proximal end of the docking station is magnetic;
   a first guidewire;
   a second guidewire;
   a third guidewire;
   a first catheter; and
   a second catheter;
   wherein the tip section is configured to:
      slidably receive the first guidewire, allowing the first guidewire to run coaxially through the tip section;
      attach to the second guidewire;
      detachably connect to the first catheter;
      magnetically dock with the proximal end of the docking section which connects to the second catheter; and
      slidably receive the third guidewire, allowing the third guidewire to run coaxially though both the tip section and the docking section; and
   wherein the system further comprises an electric hot-wire loop configured to:
      surround the second catheter;
      travel along the second catheter up to the docking section; and
      excise a substantially round section from material held between the tip section and the docking section.

10. The system of claim 9, wherein the tip section is ogive-shaped.

11. The system in claim 9, wherein the tip section and the docking section comprises material selected from a group consisting of neodymium, cobalt, iron, samarium, copper, zirconium, aluminum, nickel, and some combination thereof.

12. The system of claim 9, wherein the first guidewire has a diameter of between 0.021 inches and 0.038 inches.

13. The system of claim 9, wherein the second guidewire has a diameter of between 0.014 inches and 0.021 inches.

14. The system of claim 9, wherein the second guidewire is attached to a side of the tip section.

15. The system of claim 9, wherein the third guidewire has a diameter of between 0.021 inches and 0.038 inches.

* * * * *